US010542958B2

(12) United States Patent
Merckx (10) Patent No.: US 10,542,958 B2
(45) Date of Patent: Jan. 28, 2020

(54) METHOD AND SYSTEM FOR CONFIGURING AN X-RAY IMAGING SYSTEM

(71) Applicant: AGFA NV, Mortsel (BE)

(72) Inventor: Gert Merckx, Mortsel (BE)

(73) Assignee: AGFA NV, Mortsel (BE)

( * ) Notice: Subject to any disclaimer, the term of this patent is extended or adjusted under 35 U.S.C. 154(b) by 223 days.

(21) Appl. No.: 15/317,187

(22) PCT Filed: Jun. 12, 2015

(86) PCT No.: PCT/EP2015/063162
§ 371 (c)(1),
(2) Date: Dec. 8, 2016

(87) PCT Pub. No.: WO2015/189385
PCT Pub. Date: Dec. 17, 2015

(65) Prior Publication Data
US 2017/0119338 A1 May 4, 2017

(30) Foreign Application Priority Data

Jun. 13, 2014 (EP) .................................... 14172311

(51) Int. Cl.
*A61B 6/00* (2006.01)
*A61B 6/08* (2006.01)

(52) U.S. Cl.
CPC ............... *A61B 6/545* (2013.01); *A61B 6/08* (2013.01); *A61B 6/4464* (2013.01); *A61B 6/469* (2013.01)

(58) Field of Classification Search
CPC ....... A61B 6/0407; A61B 6/08; A61B 6/4464; A61B 6/469; A61B 6/545
See application file for complete search history.

(56) References Cited

U.S. PATENT DOCUMENTS

2004/0081341 A1* 4/2004 Cherek ................ A61B 5/0555
382/128
2008/0101538 A1* 5/2008 Schliermann ............ A61B 6/08
378/95

(Continued)

FOREIGN PATENT DOCUMENTS

EP       1 382 300 A1    1/2004
WO    2006/024622 A1    3/2006

OTHER PUBLICATIONS

Official Communication issued in International Patent Application No. PCT/EP2015/063162, dated Aug. 17, 2015.

*Primary Examiner* — David J Makiya
*Assistant Examiner* — Soorena Kefayati
(74) *Attorney, Agent, or Firm* — Keating and Bennett, LLP (57) ABSTRACT

An X-ray system for taking an X-ray image of an object includes an X-ray source, an X-ray detector, depth camera(s) covering at least an area covered by an X-ray bundle and configured to obtain depth images and a client device including a display adapted to display an impression image to a user. The system further includes a controller configured to derive the impression image including a representation of this area from the depth images; and to obtain from the client device a first geometric position correction of the X-ray imaging system with respect to this impression image; and to convert the first geometric position correction to an actual geometric position configuration of the X-ray imaging system by a known relation between the one or more depth cameras and the X-ray imaging system.

9 Claims, 8 Drawing Sheets

(56) References Cited

U.S. PATENT DOCUMENTS

| | | | |
|---|---|---|---|
| 2011/0249799 A1* | 10/2011 | Lalena | A61B 6/08 378/97 |
| 2011/0291800 A1* | 12/2011 | Butzine | A61B 6/544 340/8.1 |
| 2013/0158439 A1* | 6/2013 | Clarke | A61B 5/11 600/595 |
| 2014/0016750 A1* | 1/2014 | Kang | A61B 6/547 378/62 |
| 2015/0003674 A1* | 1/2015 | Eun | A61B 6/04 382/103 |
| 2015/0078508 A1* | 3/2015 | Lee | A61B 6/542 378/4 |
| 2015/0228071 A1* | 8/2015 | Jockel | A61B 6/08 382/132 |
| 2015/0327832 A1* | 11/2015 | Hu | A61B 6/547 378/62 |
| 2016/0113617 A1* | 4/2016 | Herrmann | A61B 6/42 378/207 |
| 2017/0035374 A1* | 2/2017 | Schafer | A61B 6/02 |
| 2017/0215823 A1* | 8/2017 | Ivanov | A61B 90/37 |

* cited by examiner

METHOD AND SYSTEM FOR CONFIGURING AN X-RAY IMAGING SYSTEM

CROSS REFERENCE TO RELATED APPLICATIONS

This application is a 371 National Stage Application of PCT/EP2015/063162, filed Jun. 12, 2015. This application claims the benefit of European Application No. 14172311.4, filed Jun. 13, 2014, which is incorporated by reference herein in its entirety.

BACKGROUND OF THE INVENTION

1. Field of the Invention

The invention relates to the field of X-ray imaging systems and more particular to the geometric configuration of X-ray imaging systems. Such a geometric configuration comprises positioning the X-ray source and X-ray detector panel with respect to an object of which an X-ray is to be taken. This positioning may be a translation of the X-ray source and detector assembly or a rotation around the object to radiate the objection from a different angle. Such a configuration may also comprise an adjustment of the diaphragm or collimator and a change of the distance between the object and the X-ray source in order to obtain a resizing or zooming effect of the X-ray image.

2. Description of the Related Art

Medical imaging systems usually include some user controls to adjust imaging parameters. The required configuration values are determined by a series of inputs, including the type of the study being performed and the characteristics of the subject being imaged. The process of selecting the right configuration given a certain subject and a desired study is crucial since this affects the image quality and the subject's wellbeing directly. In the case of X-ray imaging, for instance, image retakes caused by an erroneous configuration are especially undesirable due to the harmful nature of X-ray radiation to the subject.

In a traditional setting, the configuration is manually controlled by the operator. The radiation dose is typically derived from the medical study and the size of the subject. The position configuration of the system is typically done manually by sight, i.e., collimator setting and position of the X-ray source and detector panel are determined by the operator. However, this process is time consuming and prone to errors because the operator has no clear view of the applied adjustments. This results in an inefficient use of the X-ray system and a risk that multiple X-rays have to be captured.

Solutions have already been proposed to make the imaging process more efficient and less prone to errors.

In WO2006024622A1 an X-ray imaging system is proposed where cameras are used to capture images of the subject to be imaged. Either volume parameters are obtained from the 2D image data or a 3D model is obtained from the 2D images. From the volume parameters, X-ray imaging system's configuration is derived in an automated way. A disadvantage of this this system is that parameter extraction from the 2D images is not always correct, especially not when the cameras are under a large different angle than the X-ray emitter. Another disadvantage is that 3D model fitting from 2D images is a processor intensive operation. A further disadvantage is that an operator cannot verify the automatically derived changes without inspection of an actual taken X-ray image.

US20140016750A1 discloses an X-ray imaging system where depth cameras are used to obtain location information of the subject and to automatically position the X-ray emitter in the correction location. Also here the operator cannot verify the automatically derived changes.

SUMMARY OF THE INVENTION

The invention aims to overcome the above shortcomings and to reduce the time and effort needed to configure and fine tune an X-ray imaging system while still offering a verification to an operator.

According to a first aspect this object is achieved by a method for configuring an X-ray imaging system for taking an X-ray image of an object comprising the following steps:

Obtaining one or more first depth images of said object from one or more depth cameras. The one or more depth cameras covering at least an area covered by an X-ray bundle of an X-ray source of this X-ray imaging system in the current configuration of the X-ray imaging system.

Displaying an impression image derived from the one or more depth images on a display of a client device to a user. The impression image comprising a representation of the area covered by the X-ray bundle.

Obtaining from the client device a first geometric position correction of the X-ray imaging system with respect to this impression image.

Converting this first geometric position correction to an actual geometric position configuration of the X-ray imaging system by a known relation between the one or more depth cameras and the X-ray imaging system.

Applying the actual geometric position configuration to the X-ray imaging system.

In a depth image, a pixel represents the distance between the depth camera and a closest object in front of the camera. Otherwise put, after applying lens correction, it may be transformed to a point cloud with the position of the camera as the origin of the coordinate system. These pixels may also be assigned other attributes through combination with input from different sensors. Such pixels may be visualized as points in a three dimensional or 3D space and colourized using information from the different sensors. The impression image then gives a view of at least the area which would be imaged by the X-ray system in its current configuration, i.e., like a picture of the area was taken from a certain angle. As long as the depth cameras register the area covered by the X-ray bundle, the depth images may be transformed to an impression image by the known relationship between the X-ray source and the depth cameras.

This way, a user or operator sees the area that would be irradiated on a display and can provide corrections, i.e., the first geometric position correction. For example, if an X-ray is to be taken of a leg, the operator may notice that the leg is not completely inside the irradiation area of the X-ray source and thus specify that a translation correction needs to be applied. As the corrections are defined according to the displayed impression image, the corrections are relative to the displayed impression image and still need to be converted to an actual configuration of the X-ray system which is done in the converting step. After the converting, the configuration is applied the X-ray system.

Optionally, this method may be performed iteratively, i.e., after the applying a new set of depth images is taken to generate a new impression images in order to verify that the configuration is correct.

It is an advantage that the impression image is derived from depth images as it allows generating a field of view of the irradiated area other than the field of view of the cameras. It even allows generating a field of view that cannot be achieved by taking an image directly with a camera. Depth images further allow generating the impression image without fitting of 3D models or surfaces. It suffices to change the view point of the point cloud which is implicitly present in a depth images. To avoid missing certain points in the point cloud or depth image, multiple depth cameras may be used.

It is a further advantage that an operator does not have to be present at the X-ray system itself for the configuration. When the object has been put in front of or under the X-ray source, the operator may perform the configuration and image taking from the same client device. This allows a faster acquisition of X-ray images and a more economic use of the X-ray system.

According to an embodiment the obtaining from the client device further comprises:
Receiving an interaction of a user with the display as the first geometric position correction.

If the display is a touch display, the user may thus interact directly with the display resulting in a pleasant and interactive experience. The user may also interact indirectly with the display, for example by using an interface device such as a mouse.

Advantageously, a field of view of the impression image comprises a field of view of the X-ray source.

This way, the impression image provides a good idea of how the X-ray image would look like as it is like the impression image was taken by a camera which is in the same position as the X-ray source. Preferable, the angle of view of the impression image is larger than the angle of view of the X-ray thereby providing a view to the user of what falls outside of the area.

Another advantage is that is allows performing the converting in an easy and straightforward manner as a movement on the display directly corresponds to a movement of the X-ray source in an plane orthogonal to the optical axis of the X-ray source.

According to an embodiment the displaying comprises displaying a target area indicative for the area covered by the X-ray bundle on the impression image. The obtaining then comprises receiving a repositioning of the target area with respect to the impression image as the first geometric position correction.

The display thus not only displays an image of the area that would be irradiated by the current configuration, i.e., the impression image, but also displays a target area as the area that should be irradiated after the configuration has been applied. This may for example be done by overlaying a rectangle on the impression image. The repositioning and thus the correction is then defined by repositioning this overlay on the impression image. This may also be done the other way around, i.e., by repositioning the impression image on the display with respect to the overlay and thus the target area. If the object is represented within the impression image, the object may be repositioned with respect to the target area to achieve repositioning.

This way the correction is defined in an easy and interactive way whereby the effect of the correction is directly visible on the display before it has been applied.

According to an embodiment the first geometric position correction comprises a first translation position correction of the X-ray system. The actual geometric position configuration then comprises an actual translation position configuration of the X-ray system and the converting comprises converting this first translation position correction to this actual translation position configuration of the X-ray imaging system.

In other words, the user thus performs a pure translation correction, i.e., a correction in a plane defined by the impression image. This may for example be done by shifting the impression image or target area on the display. Advantageously, the interaction is done by a panning operation performed on the display as this first translation position correction. In the case of touch display this may be done by a panning operation with a finger on the display. Alternatively, this may be done performing the panning with an interface element such as a mouse.

A translation correction will also result in a translation of the X-ray source, preferably together with the detector panel.

The first geometric position correction may also comprise a first rotational position correction of the X-ray system and the actual geometric position configuration comprises an actual rotational position configuration of the X-ray system. The converting then comprises converting this first rotational position correction to this actual rotational position configuration of the X-ray imaging system.

In other words, even if the object is in the correct location for irradiation, it may still be desired that the object is irradiated from another angle. The change in angle is then defined by the rotational position correction. The actual rotational position configuration will then comprise a translation and rotation of the X-ray source in order to obtain the rotation correction.

Advantageously, the interaction then comprises a rotational operation performed on the display as the first rotational position correction, i.e., by a direct or indirect interaction with the screen.

The correction may further be visualized to the user by an actual rotation of the impression image, i.e., by generating a new impression image as if the correction was applied. This provides the user a good view of the result of the correction before applying the actual rotational position configuration.

The first geometric position correction may also comprise a first resizing position correction and the actual geometric position configuration may comprise a diaphragm configuration of the X-ray system. The converting then comprises converting this first resizing position correction to this diaphragm configuration of the X-ray imaging system.

The user thus indicates that a smaller or larger area should be irradiated which is similar to a resizing of the area covered by the X-ray bundle. This will thus result in a zooming effect on the final X-ray image. In digital terminology, this would be referred to as digital zooming. To accomplish this, the diaphragm or collimator of the X-ray source is changed in order to irradiate the resized area.

Alternatively or complementary, the first geometric position correction comprises a first resizing position correction and the actual geometric position configuration comprises a distance configuration of the object with respect to the X-ray source and a detector panel of the X-ray system. The converting then comprises converting the first resizing position correction to the distance configuration.

A similar resizing of the irradiation area is thus achieved by adjusting the position of the object with respect to the X-ray source and the detector panel along the optical axis of the X-ray source. This also results in the effect that a larger or smaller portion will be irradiated and thus the zooming effect of the final X-ray image is accomplished.

In both cases, the interaction may comprise a resizing operation of the target area or of the impression image performed on the display as the first resizing position configuration. Advantageously, this resizing operation is a pinching operation performed on the display.

The user thus defines the resizing position correction by interaction with the display. Either the impression image is resized while the target area remains the same, either the target area is resized while the impression image remains the same. The change in size of the impression image or target area is then a measure for the first resizing position correction.

It is an advantage that all type of corrections, i.e., translation, rotation and resizing, can be easily defined by a user through an interaction with the display based on the impression image. By the various embodiments, also the result of the corrections is already directly visible on the display, either by a change in the impression image or a change in the target area.

The object may be part of a bigger object. In this case, the method may further comprise:
  Determining a geometric position of the bigger object in the impression image.
  Presenting an overlay of the bigger object on the impression image.
The receiving a repositioning of the target area with respect to the impression image then comprises receiving a repositioning of this overlay of the bigger object with respect to the target area.

It may be the case that the object or part of the object of which an X-ray image is to be taken falls outside the field of view of the depth cameras. For example, an X-ray image of a leg is to be taken but the depth camera only captures the upper part of the body. In this case, the upper part of the body is recognized and an estimation of the rest of the body is displayed on top of the impression image in the form of an overlay. The estimation itself is obtained from prior knowledge of the object of bigger object. The user can then reposition the overlay with respect to the impression area or the target area until the object of which an estimation is shown in the overlay is displayed in the target area. The repositioning of the overlay is then a measure for the correction to be applied.

This may occur when the X-ray system is still in its previous configuration where an image was taken of another object, for example a body part of a previous patient. By the overlay of the bigger object, e.g. a complete body of a patient when an image of a leg is to be taken, the user may perform a first rough configuration of the X-ray system in order to get the leg within the view of the depth camera(s) and thus within the impression image.

According to an embodiment, the object or the bigger object may also comprise a skeleton and joints. The method then further comprises:
  Determining a position of these joints from the impression image or the depth images.
  Overlaying the impression image with an estimated image of said object by a known position relation between these joints and said object.
This is particularly useful when the object is not visible which is often the case in X-ray imaging where, for example, the object is a bone structure or an organ. The joints can be identified directly from the impression image or from the depth images by image recognition algorithms. The estimation image is then a rendering of the object in the correct location thereby giving the impression of an X-ray image and thus providing a good idea of the final result.

According to a second aspect, the invention relates to an X-ray system for taking an X-ray image of an object comprising:
  An X-ray source and X-ray detector.
  One or more depth cameras covering at least an area covered by an X-ray bundle of the X-ray source and configured to obtain one or more first depth images.
  A client device comprising a display adapted to display an impression image to a user.
  A controller configured to:
    Derive this impression image comprising a representation of the area covered by the X-ray bundle from the one or more first depth images.
    Obtain from the client device a first geometric position correction of the X-ray imaging system with respect to the impression image;
    Convert the first geometric position correction to an actual geometric position configuration of the X-ray imaging system by an known relation between the one or more depth cameras and the X-ray imaging system;
    Apply the actual geometric position configuration to the X-ray imaging system.

DETAILED DESCRIPTION OF THE PREFERRED EMBODIMENTS

Figure 1:
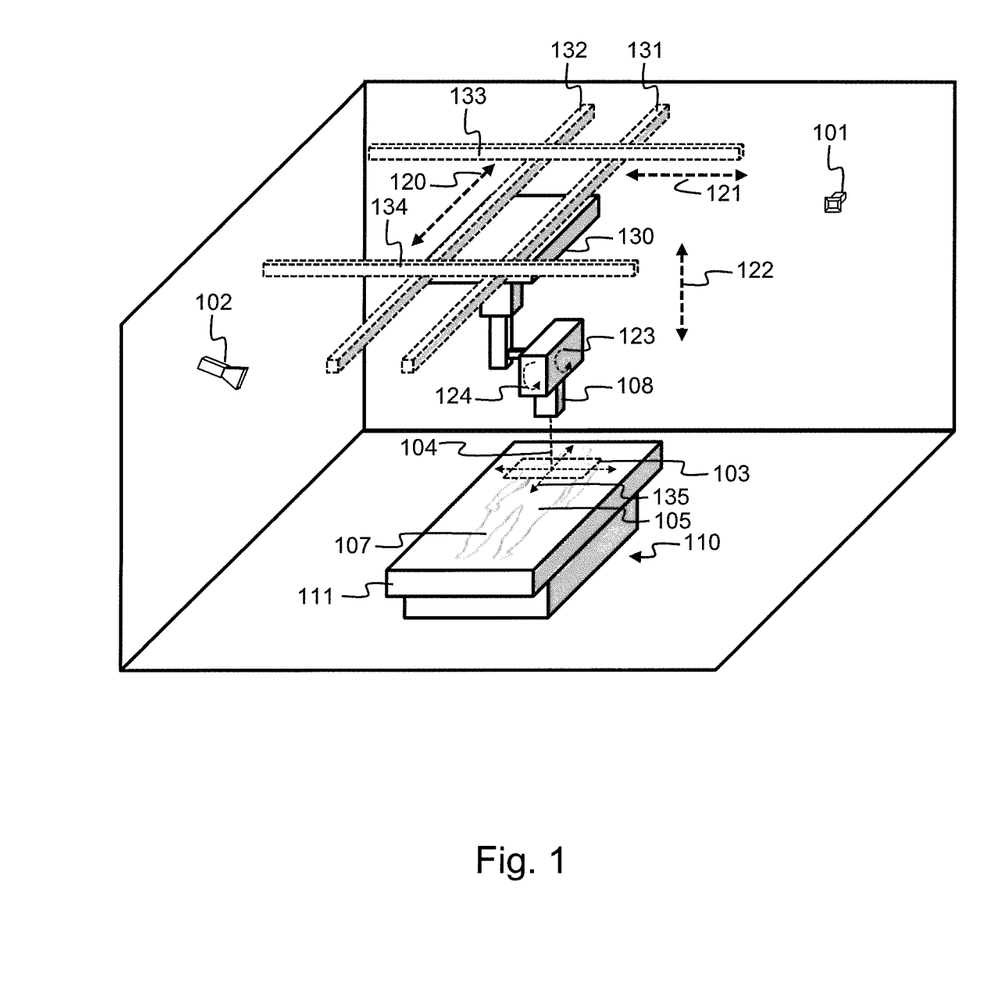
FIG. 1 illustrates parts of an X-ray imaging system according to an embodiment of the invention.

FIG. 1 illustrates parts of an X-ray imaging system according to an embodiment. The system comprises an X-ray source 108 or X-ray tube 108 to radiate a subject 105. The array 103 illustrates the area that would be radiated by the X-ray bundle from the X-ray source 108 in the illustrated setup. This bundle is emitted from the X-ray source 108 along its optical axis 104. It is an object to configure the X-ray imaging system such that the appropriate area on the subject 105 is radiated and thus imaged. The configuration of the X-ray device 100 will be illustrated in the embodiments below for the case where an object 107, i.e., the knee of the subject 105, i.e., a person, is to be imaged. According to the example, it is thus the object to have the object 107 within the X-ray bundle, i.e., within the area 103. The X-ray bundle is then detected by an X-ray detector panel 111 behind the subject 105. Such a detector panel may for example be a digital flat panel detector for directly capturing a digital version of the image.

The X-ray imaging system comprises several ways of configuration in order to manipulate or change the radiated area 103 and thus the field of view of the X-ray image. The configuration of the X-ray imaging system defining the radiated array on the subject 105 is further referred to as the geometric configuration or geometric position configuration of the X-ray imaging system. It is an object to define a geometric position configuration such that the object 107 is correctly imaged and thus radiated by the X-ray imaging system.

A first type of geometric position configuration of the system is a translational movement 135 of the X-ray source 108 with respect to the subject and more specifically in a plane parallel to the detector 111, i.e., a translation configuration of the X-ray imaging system. In the system of FIG. 1, such a translational movement or translational position configuration may be accomplished by a movement of the X-ray source 108 supporting assembly 130 along the guides 131 till 134. The guides 131 and 132 allow a movement in a first direction 120 and the guides 133 and 134 allow a movement in a second direction 121. Any combination of movements along these two directions 120 and 121 then define a translational position correction of the X-ray source 108. A translational position configuration may also be done by a movement of the supporting table 110 on which the subject 105 is positioned. A translational movement may also be done by a combination of a movement of the X-ray source 108 and a movement of the supporting table 110. A translational movement of the X-ray source with respect to the subject 105 will result in a repositioning of the radiation area 103 on the subject.

A second type of geometric position configuration of the system is a rotational position configuration whereby the X-ray source 108 rotates with respect to the subject 105 in order to image the object 107 from a different angle. Preferably, the X-ray source then rotates around the point where the optical axis 104 crosses the surface of the subject 105 resulting in a pure change in viewing angle without changing the field of view itself. This may be accomplished be a rotation of the X-ray source around itself combined with a movement of the X-ray source along the three directions 120, 121 and 122. This may also be accomplished by a small rotation of the supporting table 110 or by a combined movement of the supporting table 110 and the X-ray source 108.

A third type of geometric position configuration is the configuration of the collimator or diaphragm. Typically such collimator is in front of the X-ray source and limits the X-ray bundle to a certain shape. This allows resizing the radiation area 103 on the subject 105 and thus limiting the amount of received radiation to the subject.

A fourth type of geometric position configuration is the configuration of the distance of the X-ray source 108 to the subject 105 and thus to the object 107, i.e. a distance configuration of the X-ray imaging system. The closer the X-ray source is to the subject 105, the smaller the radiated area 103 becomes. This distance configuration may be accomplished by moving the X-ray source, the supporting table 111 or both along the axis 122.

The X-ray imaging system according to the embodiment further comprises depth cameras 101 and 102. The depth camera are positioned and configured such that their field of view comprises the area 103 captured by the X-ray source 108. According to further embodiments, the depth cameras are used for configuring the X-ray system.

Figure 2:
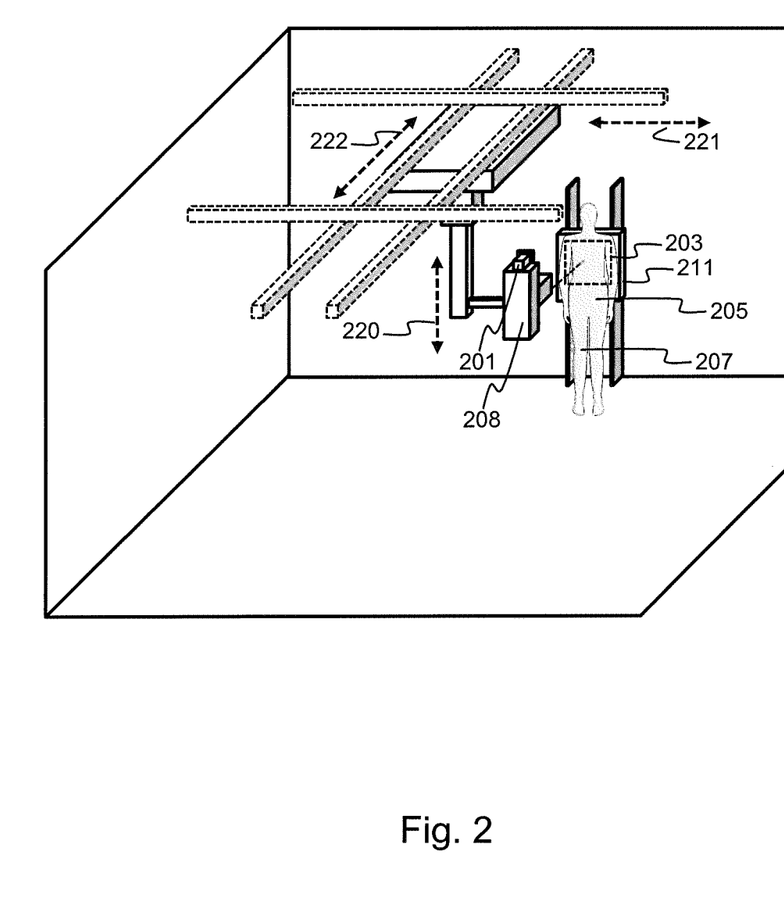
FIG. 2 illustrates parts of an X-ray imaging system according to an embodiment of the invention.

FIG. 2 illustrates parts of an X-ray imaging system according to an alternative embodiment. The X-ray detector panel 211 is in a vertical position and the subject 205 stands in an upright position against the detector panel. For the translational movement, the X-ray source 208 moves together with the detector panel 211 along the directions 222 and 221. For the distance configuration the X-ray source moves along the direction 222 further or closer to the subject 205 and thus the object 207. Also here, the area 203 covered by the X-ray bundle in the current setup of the X-ray system is shown on the subject 205. The X-ray system may further also allow configuring the collimator or diaphragm in the X-ray source 208. Attached to the X-ray source 208 is a depth camera 201 covering at least the area 203. Preferably, the optical axes of the X-ray source 208 is aligned or substantially parallel to the optical axis of the depth camera 201.

Figure 8:
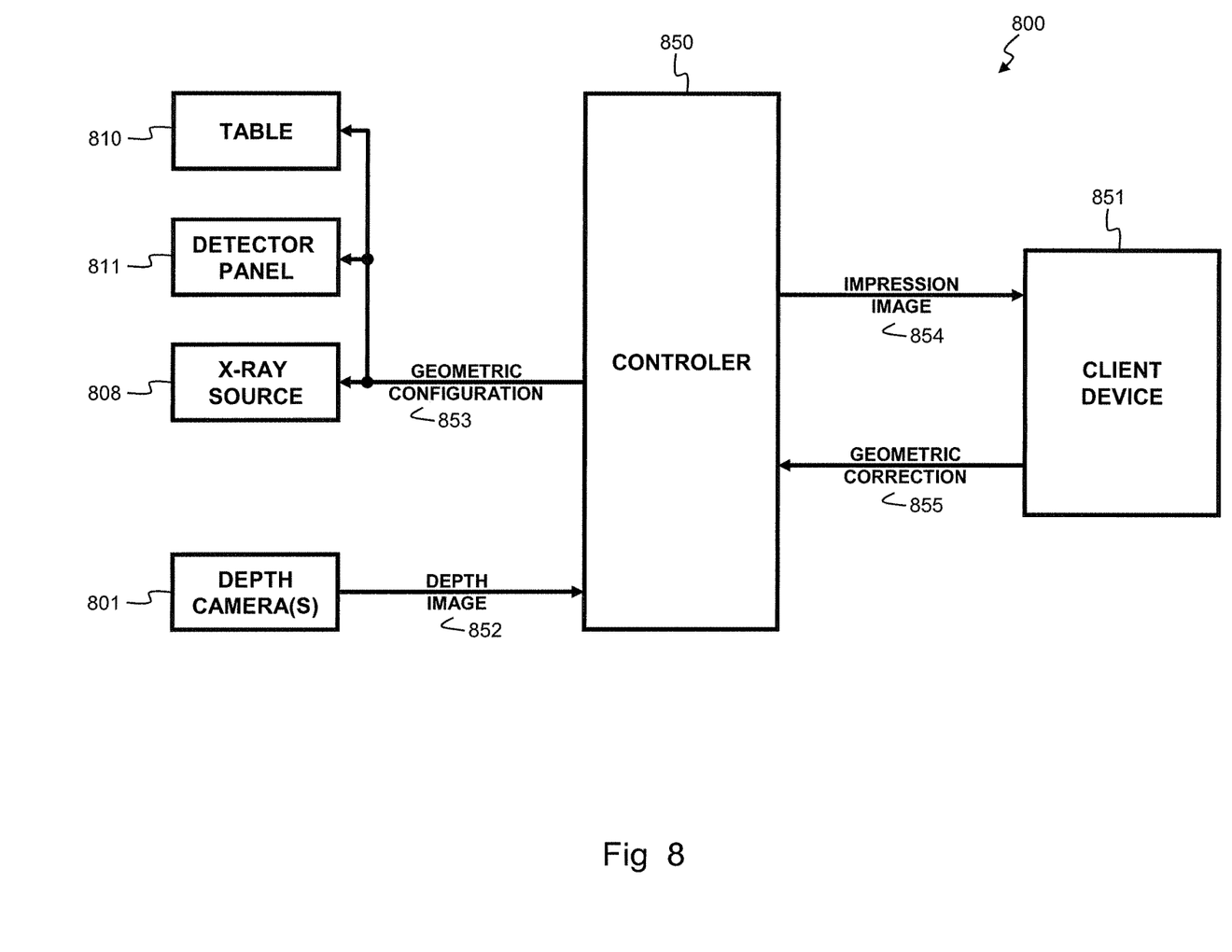
FIG. 8 illustrates a schematic view of an X-ray imaging system according to an embodiment of the invention.

FIG. 8 gives a schematic overview of an X-ray imaging system 800 comprising the X-ray imaging parts as shown in FIG. 1 and FIG. 2. According to an embodiment of the invention. It comprises the X-ray source 808 corresponding to the X-ray source 201 or 101, a detector panel 811 corresponding to the detector panel 111 or 211 and optionally a table 810 if according to FIG. 1. If an X-ray image is to be taken of an object 107 or 207, the components 810, 811 and/or 808 need to be configured appropriately, i.e., a geometric configuration 853 needs to be defined that is then applied to these components. This geometric configuration 853 is calculated by the controller 850. In order to do so, the controller 850 receives one or more depth images 852 from the depth camera(s) 801. From these depth images 852 the controller derives an impression image 854. This impression image is, on its turn, sent to a client device 851. By interaction with a user, the client device then obtains a geometric correction 855 with respect to the impression image 854 and sends it to the controller 850. The controller then derives the appropriate geometric configuration 853 from the received correction 855 and the known relationship between the components 810, 811 and/or 808 and the depth camera(s) 801. The functionality and logic resource of the controller 850 may also be implemented in the client device 851.

The depth images 852 are a 2D image where each point in the image represents a distance value between the depth camera 801 and the subject in front of it. The depth images 852 may be combined with colour or infrared sensor information. The depth image may also be transformed to a point cloud where each point of the image is represented by a 3D coordinate.

The impression image is a conventional colour or greyscale image of the subject 105, 107 as seen from a certain angle of view and is obtained by the controller 850 from the one or more depth images 852. The impression image preferably has at least the angle of view of the X-ray source 808 in its current setup, i.e., it is like the impression image was taken with a camera with the same optical axis as the X-ray source 808 and with at least the same viewing angle. This way, the impression image gives the impression of what information the x-ray image would contain if taken in the current configuration.

In the case where the depth camera is aligned with the optical axis of the X-ray source such as with the depth camera 201 of FIG. 2, the impression image can be directly obtained from the depth image as long as the area 203 is within the field of view of the depth camera 201. If colour attributes are present in the depth image, these may be used for the impression image, otherwise the depth distance values in the image can be converted to a grayscale or colour value.

In the case where more than one camera is used or when a camera is not aligned with the optical axis of the X-ray source such as illustrated by FIG. 1, the impression image cannot be directly obtained from the depth image. In this case, the depth images are converted into a point cloud by representing each point as a three dimensional coordinate in a coordinate system fixed to the respective depth camera. Optionally, each point may also comprise a colour or grayscale value. In a next step, the point clouds obtained from each depth images are then merged into a single point cloud. This can be done be transforming the coordinate systems of each point cloud to a single fixed coordinate system relative to the X-ray imaging source. For the transformation, the known position relationship between the depth cameras and the X-ray source is taken into account. From the single point cloud image, the impression image is then derived by generating a view from the point cloud where the X-ray source is and along the optical axis of the X-ray source.

The impression image 854 may also be derived indirectly form the depth image(s) 852 by making use of an anatomical model and/or a model of the X-ray imaging system. In this case, the controller has a stored three dimensional anatomical model of a standard subject. From the depth image(s) or point cloud, it retrieves the position, size and orientation of the subject and then transforms the anatomical model such that it fits the derived parameters of the subject. Then, the controller renders an image as a view from a certain viewing angle of this anatomical model thereby obtaining a rendered impression image. In other words, the controller 854 obtains a three dimensional model of the subject and then renders the impression image from this model. Since the depth data may be incomplete, this has the advantage that it provides a greater flexibility in the generation of the impression images, but, on the other hand, the impression image may look less realistic.

When using the anatomical model, also a model of the X-ray imaging system may be used for the generation of the rendered impression image. In this case, a three dimensional model of the X-ray imaging system is available in the controller 854. The controller then positions the X-ray imaging system in its current configuration in this model and also places the transformed anatomical model of the subject within the model of the X-ray imaging system. Combined with the depth images, a complete three dimensional model of the X-ray imaging system in its current configuration and the subject is then available. Then, the controller renders a view of the subject from this complete model as the rendered impression image. This provides an even more realistic view.

Figure 3:
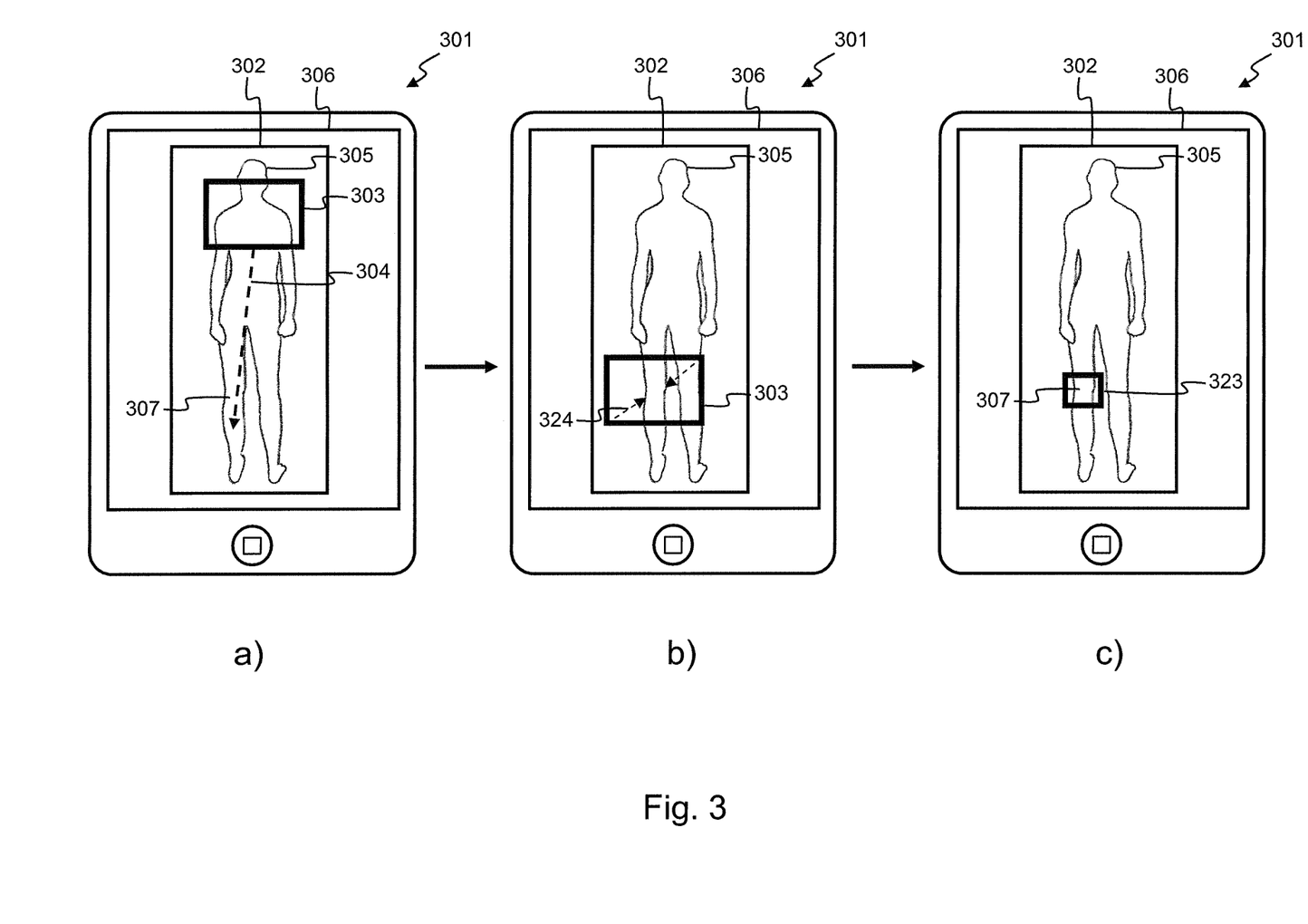
FIG. 3 illustrates steps performed on a client device in order to obtain a geometric position correction of an X-ray imaging system according to an embodiment.

FIG. 3 illustrates how the geometric correction 855 is defined on the client device 301 according to an embodiment. The client device 301 is touch device with a touch screen or display 306, for example a capacitive touch screen. On the screen, the obtained impression image 854 from the controller 850 is displayed to a user as the impression image 302. A target area 303 is also displayed on top of or within this impression image 302. This target area 303 defines the current area on the subject 305 covered by the X-ray imaging system, i.e. which area would be radiated if an X-ray image would be taken in the current configuration. From the depth images, the distance between the X-ray source and the subject 305 is known. From this distance, the actual size of the X-ray bundle on the subject 305 can be derived and is shown as the target area 303. This way, the impression image 302 comprises a representation of an area covered by the X-ray bundle similar to the areas 103 and 203 in respective FIG. 1 and FIG. 2. The target area 303 may also be a part of the impression image. For example, if the impression image is a rendered impression image, the generation of the target area may be part of the rendering process. This may for example be done by introducing a lighting source at the location of the X-ray tube within the model of the X-ray imaging system when rendering the impression image. Because of the geometric configuration which is part of the model, the impression image will also comprise the target area 303 as a lighted surface on the subject.

The user of the client device 301 then repositions and resizes the target area 303 in such a way that it corresponds to a desired area 323, i.e., the area that should actually be radiated by the X-ray source and thus the area of which an X-ray image is to be taken. The desired area 323 should at least cover the object of which the X-ray image is to be taken. In the example of FIG. 3, the object is the knee 307 of a person.

FIG. 3-a) illustrates a translation of the target area 303 made by the user in order to get the object of interest, i.e., the knee 307, within the target area 303. The translation of the target may be done by a touch and dragging operation performed on the display 306 of the touch device 301 also referred to as a panning operation. For this, the user may for example use one or more fingers or a stylus. The result of the dragging operation is a translation correction 304 of the target area 303 and, thus, representing a desired correction of the X-ray imaging system. The result of the translation correction 304 is shown in FIG. 3-b) where the target area 303 is now in its new position.

Then, the user performs a resizing position correction 324 of the target area 303 as also shown in FIG. 3-b). In the example this is done by making the target area 303 smaller in order to limit X-ray radiation of the subject 305. This way the user indicates that the X-ray radiation should be limited to the area on the subject 305 defined by the resized target area 323. As the device 301 is a touch device, this resizing position correction 324 may be done by an interaction of the user with the touch screen 306. When making the target area 303 bigger, a zooming operation may be used and when making the target area 303 smaller a pinching operation may be used. The result of the resizing position correction 324 is shown in FIG. 3-c).

Figure 4:
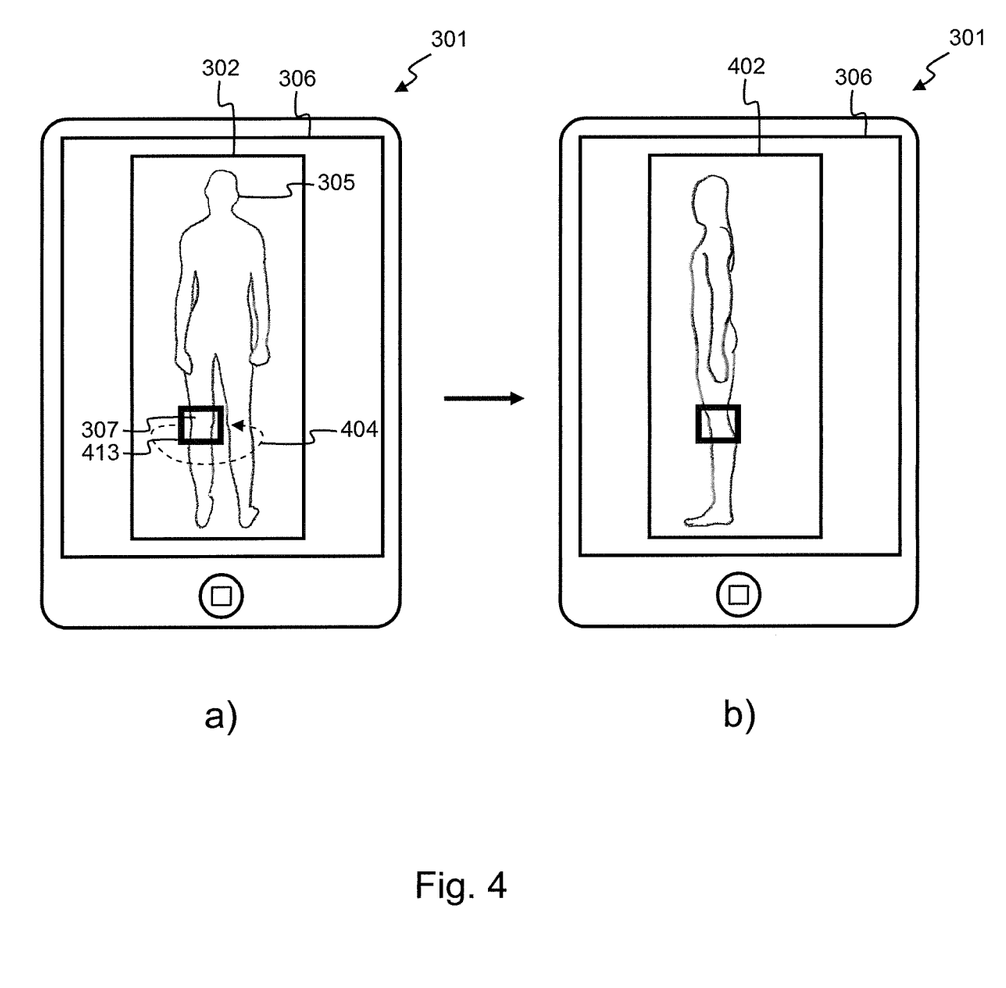
FIG. 4 illustrates steps performed on a client device in order to obtain a rotational position correction of an X-ray imaging system according to an embodiment.

A third geometric position correction of the X-ray imaging system that may be performed by means of the client device is a rotational position correction 404 as illustrated by FIG. 4. In FIG. 4-a) the target area 413 on the impression image 302 is shown as obtained in FIG. 3-c). The user then defines a rotation of the target area 413 around the subject 305 and thus around the object 307 that is to be imaged. The rotation correction thus defines a different angle from which the object 307 in the area 413 is to be imaged. This correction may be defined by a rotation operation of the user on the touch screen 301. In response to this rotation operation, the client device 301 then rotates the impression image 302. In order to do so, a new impression image 402 is derived from the one or more depth images in order the obtain an image 402 as if it was taken from an angle after the rotation operation is applied. FIG. 4-b) illustrates the result of the rotation position correction 404 on the display 306 of the touch device 301.

Figure 5:
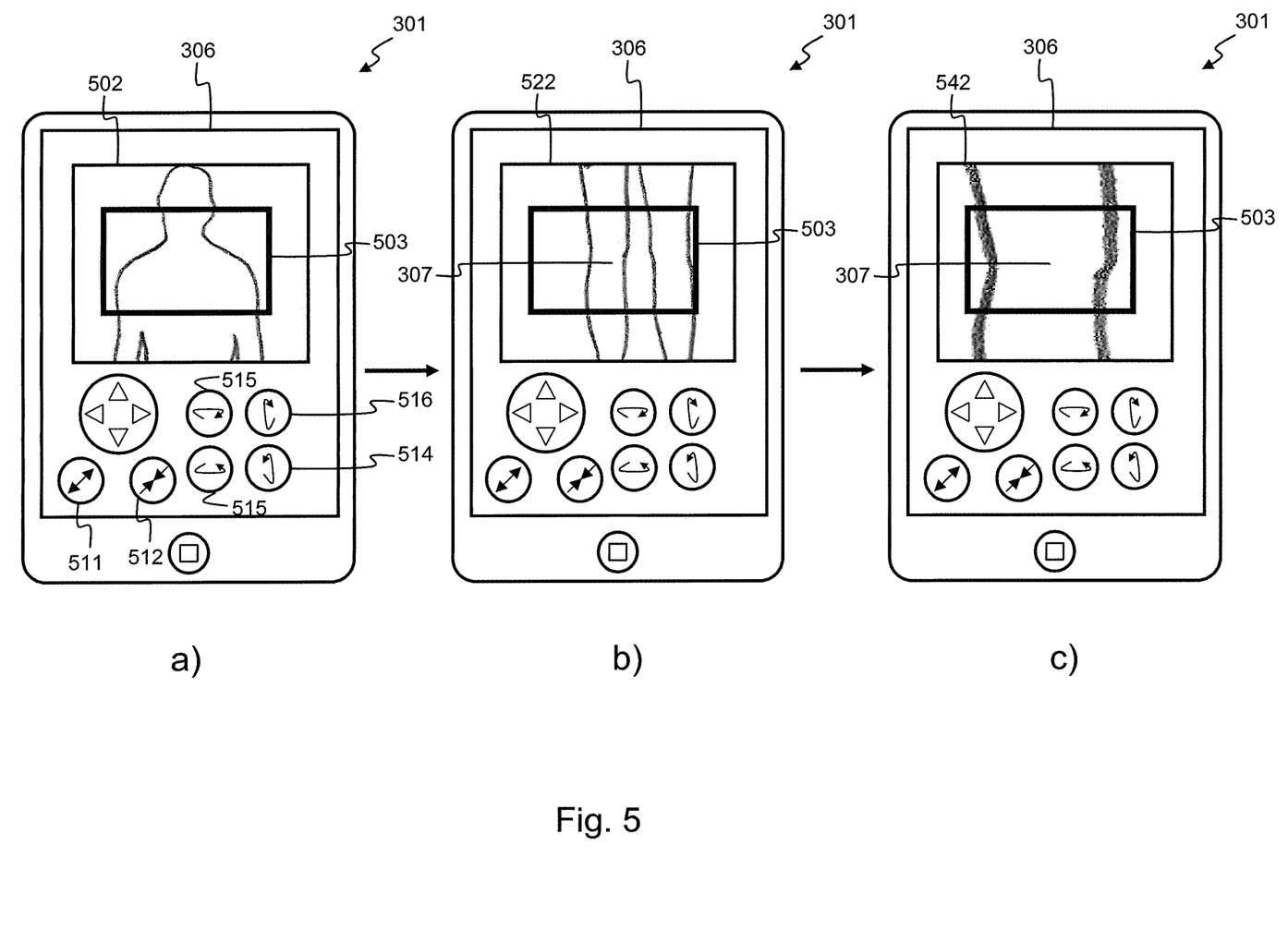
FIG. 5 illustrates steps performed on a client device in order to obtain a geometric position correction of an X-ray imaging system according to an embodiment.

According to the embodiments of FIGS. 3 and 4, the client device 301 obtains a geometric position correction comprising a translation position correction 304, a resizing position correction 324, and a rotation position correction 404. The user inputs in order to define the corrections may alternatively also be obtained by buttons displayed on the screen 302 of the touch device 301. This is illustrated in FIG. 5. The pad 510 may be used for the translation position correction 304, the resizing buttons 511 and 512 for the resizing position correction and the rotation buttons 513 till 516 for the rotation position correction. The client device may also have a keyboard or mouse and the corrections may then be obtained by inputs from the keyboard or mouse.

FIG. 5 further shows an alternative way to visualize the corrections on the display 306 of the client device 301. In FIG. 5-a) the initial impression image 502 is displayed together with the target area 503. The target area now has a fixed position on the screen but the impression image 502 will be moved or modified based on the user inputs. FIG. 5-b) shows the result of a translation correction. The impression image 502 has been updated to the image 522 by a visual translation to reflect the translation correction applied by the user. By this translation, the object 307, i.e., the knee, is now within the target are 503. FIG. 5-c) then shows the result of a further resizing position correction performed by a resizing operation by the user. This resizing operation may for example be performed by a pinch or zoom operation on the touch screen 306 or by the resizing buttons 511 and 512. In this case the impression image 522 is magnified in order to reflect the zooming operation defined by the user resulting in the magnified impression image 542. By the resizing position correction, the imaging area corresponding to the target area 503 is now restricted to the object 307 thereby limiting exposure to the X-rays.

According to a further embodiment, when the client device is using a rendered impression image, the impression image is re-rendered together with the target 503 area while the user performs the corrections. In this case, a performed correction on the client device 301 is transformed to a geometric configuration of the X-ray imaging system. This configuration is then applied to the model of the X-ray imaging system and a new impression image comprising the target area is rendered from the updated model. This re-rendering of the impression image may further be performed in real-time thereby providing a smooth user experience.

The geometric position corrections define the desired relative movement between the object and the target area representing the current configuration of the X-ray imaging system. This desired relative movement thus defines the desired geometric reconfiguration of the X-ray imaging system. Because of the predefined position relation between the X-ray imaging system and depth cameras, the geometric reconfiguration of the X-ray imaging system may be derived by the geometric position corrections performed on the impression image or target area.

From the translation correction 304, the translation configuration of the X-ray imaging system is calculated. A translation is then a three dimensional movement of the X-ray source with respect to the object 307. This may be accomplished by moving the X-ray source and detector with respect to the object, by moving the object with respect to the X-ray source or by a combination of both. When performing a translation configuration a coordinate system fixed to the X-ray source does not rotate with respect to a coordinate system fixed to the object 307. Advantageously the derived impression image has at least the field or angle of view of the X-ray source. In this case, the virtual optical axis of the impression image is substantially identical to the optical axis of the X-ray source. In other words, the target area in the impression image, provides the same field of view as when the reconfigured X-ray system would have taken the image. In such a case the translation between the translation correction and the translation configuration of the X-ray imaging system are defined in the same plane, i.e., the plane orthogonal to the optical axis of the X-ray source.

From the rotational correction 404, a rotational configuration of the X-ray source is derived. To perform the rotational correction 404, the X-ray source needs to rotate around the object 307 and thus around the target area 303. After this rotation, the X-ray source still needs to be at the same distance from the object 307 as before the correction. The rotational configuration will result in the combination of the translation and a rotation of the X-ray source. Alternatively, the same effect may be achieved by a pitch and/or roll and/or yaw movement of the subject or the surface on which the subject is positioned.

The resizing correction 324 may be applied by two configuration possibilities of the X-ray imaging system. A first possibility is by adapting the collimator size or aperture of the X-ray source. By making the aperture of collimator smaller, the radiated area will be smaller; and by making it bigger, the radiated area will be greater. The opening of the collimator and thus the configuration of the collimator is directly related to the size of the target area and the distance between X-ray source and the object. The size of the target area is defined by the user on the client device 301 and the distance may be derived from the depth images. This way, the collimator configuration is derived from the resizing correction 324.

A second configuration possibility to apply the resizing operation 324 is by changing the distance between the X-ray source and the object 307. By decreasing the distance, the target area will become smaller and by increasing the distance, the target area will become bigger. Therefore, the distance configuration between the X-ray source and the object 307 is derived from the current distance and the resizing operation 324, i.e., the change in size of the target area with respect to the object 307.

The two above configuration possibilities may also be combined in order to achieve the desired resizing correction 324. Preferable, the correction is achieved by changing the opening of the collimator. The distance configuration is then only applied when the collimator of already at its widest setting.

Figure 6:
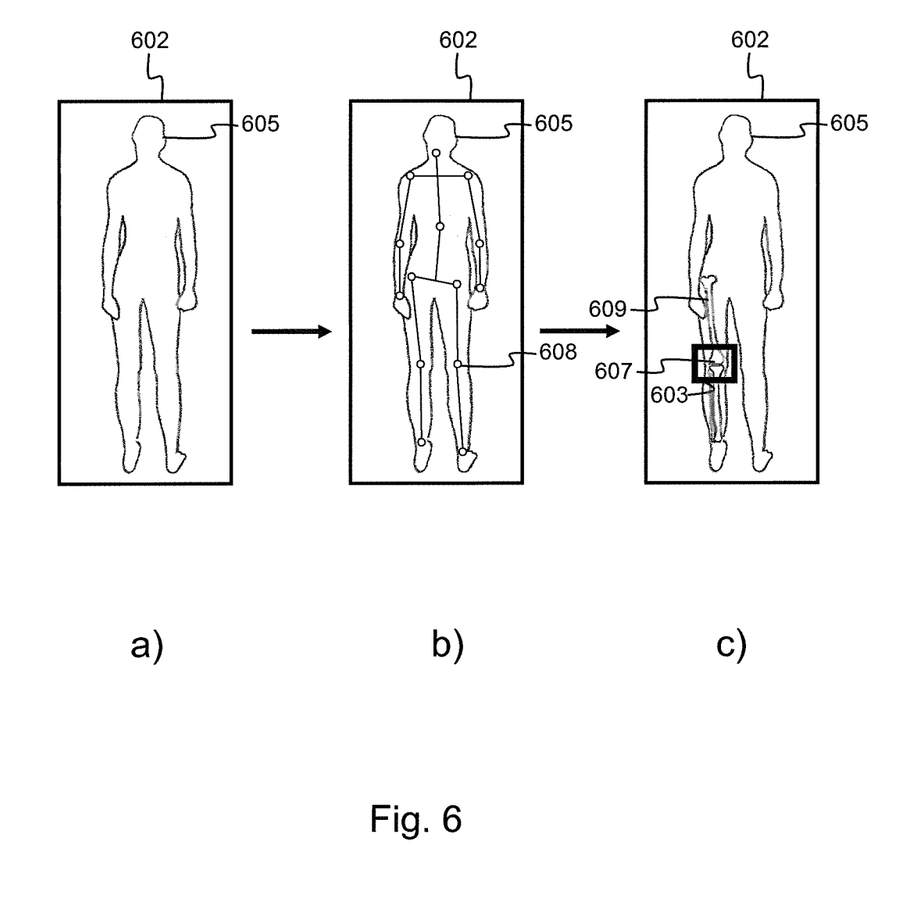
FIG. 6 illustrates steps to overlay an impression image with a bone structure or skeleton according to an embodiment.

In general, an X-ray image is taken to obtain information about an inner object of a person such as for example a bone or an organ. In such a case, the object itself will not be visible on the impression image. FIG. 6 illustrates further steps performed with the impression image on the client device in order to define the desired target area more accurately. When the depth image is obtained of a person 605, the location of the joints 608 are identified in the depth image. This may for example be done by sensor middleware software as available on the market such as the Microsoft Kinect Software Development Kit or SDK. From the location of the joints 608, an anatomical model is transformed to match the pose of the subject, i.e., of the identified joints 608. This model may comprise bones, organs and other tissue types of which the object 607. From the model, the location of the object 607 is then known and a rendering 609 is then overlaid on the impression image. In the example of FIG. 6, a skeleton or part of the skeleton 609 comprising the object 607 is overlaid on or rendered within the impression image 602. This allows the user or operator to define the target area 603 more accurately and thus to irradiate less healthy tissue. The overlay of bones 609 may also be used if images of organs are to be taken. In general, the location of organs is better known with respect to the bones than it is with respect to an image of a person. The client may further indicate the position of the organ by retrieving the position of the organ with respect to the bone structure from an image database.

Figure 7:
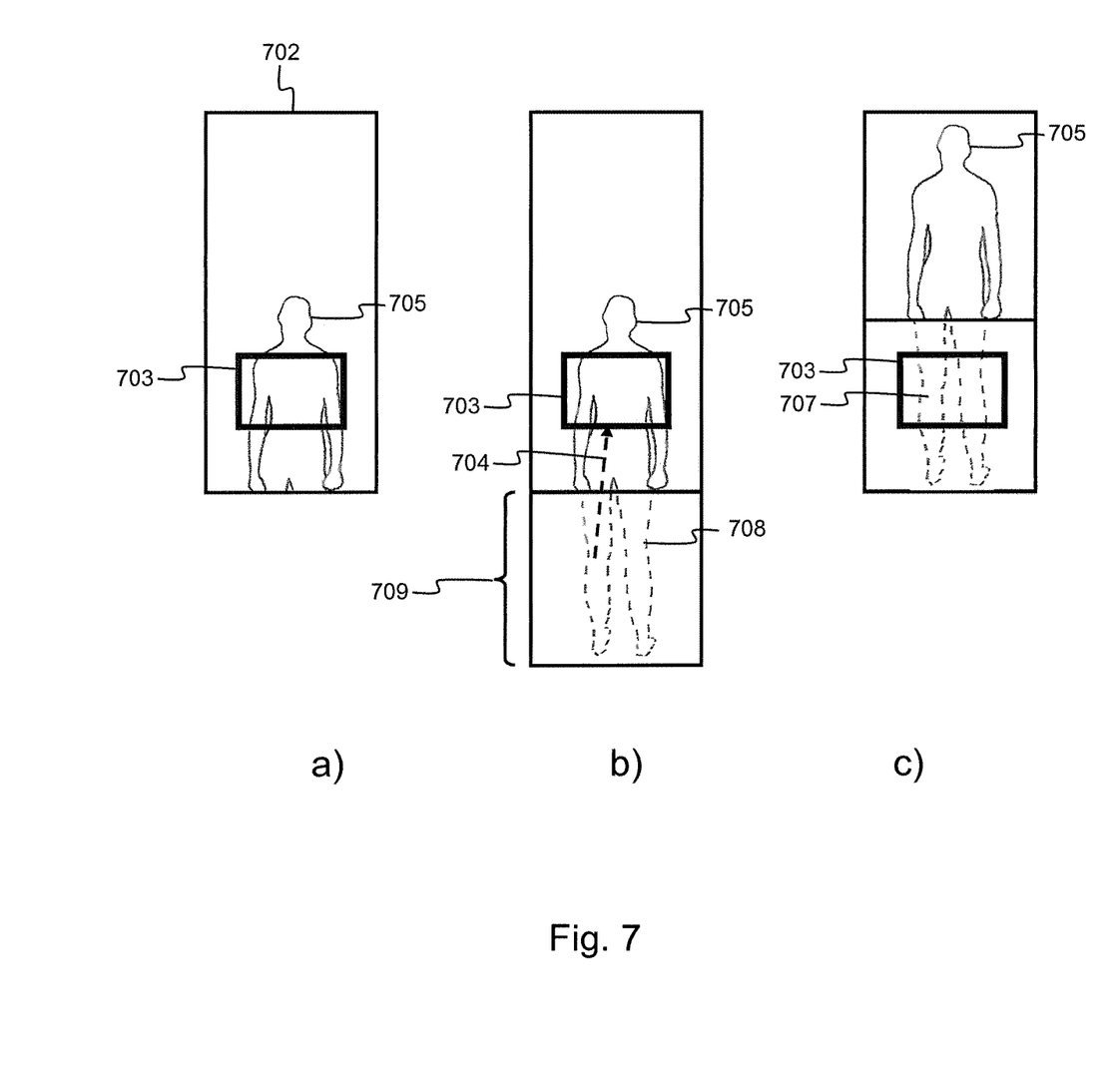
FIG. 7 illustrates steps performed on a client device in order to extrapolate an impression image according to an embodiment.

FIG. 7-*a*) illustrates a situation where the impression image 702 does not cover the object 707. The user would thus not be able to move the object in the target area. This may be the case when the X-ray imaging system is still in a position defined for a previous subject. In order to avoid a coarse manual correction and thus configuration, the steps according to FIG. 7-*b*) and -*c*). In the first step b), an image recognition algorithm recognizes the part of the subject 705 that is within the impression image and extrapolates the remainder 708 of the subject 705 as an additional image 709. When the user then moves the impression image 702 as shown in step c) and according to the embodiment of FIG. 5 into the target area 703, the client will show a part of or the complete additional image 709 on its display. The movement 704 of the impression image together with the additional image 709 then defines the translation correction of the X-ray imaging system.

When, according to the above embodiments, the geometric position configuration of the X-ray imaging system is calculated based on the corrections of the user on the client device, then the configuration is applied to the X-ray imaging system. The system then moves to the appropriate position. The procedure according to the above embodiments may then be repeated in order to fine-tune the corrections.

The calculating of the configuration and the applying thereof may also be done in real-time, i.e., while the user changes the position of the impression image or target area:
The configuration is calculated and applied
New depth images are taken
A new impression image is shown on the display
Also these step may for example be performed every 100 ms thereby providing the user with a real-time and smooth view of the X-ray imaging system.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", "third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A method for configuring an X-ray imaging system for taking an X-ray image of an object, the method comprising the steps of:
   obtaining one or more first depth images from one or more depth cameras, the one or more depth cameras covering at least an area covered by an X-ray bundle from an X-ray source;
   displaying an impression image derived from the one or more first depth images on a display of a client device to a user, the impression image including a representation of the area covered by the X-ray bundle;
   obtaining from the client device a first geometric position correction of the X-ray imaging system with respect to the impression image;
   using the first geometric position correction to calculate an actual geometric position configuration of the X-ray imaging system based on a predetermined positional relationship between the one or more depth cameras and the X-ray imaging system; and
   applying the actual geometric position configuration to the X-ray imaging system; wherein
   the step of obtaining from the client device further includes receiving an interaction by the user with the display as the first geometric position correction;
   the first geometric position correction includes a first translation position correction of the X-ray system;
   the actual geometric position configuration includes an actual translation position configuration of the X-ray system;
   the step of using includes using the first translation position correction to calculate the actual translation position configuration of the X-ray imaging system; and
   the interaction includes a panning operation performed on the display as the first translation position correction.

2. The method according to claim 1, wherein the step of displaying includes displaying a target area indicative of the area covered by the X-ray bundle on the impression image; and
   the step of obtaining further includes receiving a repositioning of the target area with respect to the impression image as the first geometric position correction.

3. The method according to claim 2 wherein the object is a portion of a bigger object; and
   the method further comprises the steps of:
   determining a geometric position of the bigger object in the impression image;
   presenting an overlay of the bigger object on the impression image; wherein
   the step of receiving the repositioning of the target area with respect to the impression image includes receiving a repositioning of the overlay of the bigger object with respect to the target area.

4. A method for configuring an X-ray imaging system for taking an X-ray image of an object, the method comprising the steps of:

obtaining one or more first depth images from one or more depth cameras, the one or more depth cameras covering at least an area covered by an X-ray bundle from an X-ray source;

displaying an impression image derived from the one or more first depth images on a display of a client device to a user, the impression image including a representation of the area covered by the X-ray bundle;

obtaining from the client device a first geometric position correction of the X-ray imaging system with respect to the impression image;

using the first geometric position correction to calculate an actual geometric position configuration of the X-ray imaging system based on a predetermined positional relationship between the one or more depth cameras and the X-ray imaging system; and applying the actual geometric position configuration to the X-ray imaging system; wherein the step of obtaining from the client device further includes receiving an interaction by the user with the display as the first geometric position correction;

the first geometric position correction includes a first rotational position correction of the X-ray system;

the actual geometric position configuration includes an actual rotational position configuration of the X-ray system;

the step of using includes using the first rotational position correction to calculate the actual rotational position configuration of the X-ray imaging system; and the interaction includes a rotational operation performed on the display as the first rotational position configuration.

5. The method according to claim 4, wherein the step of displaying includes displaying a target area indicative of the area covered by the X-ray bundle on the impression image; and the step of obtaining further includes receiving a repositioning of the target area with respect to the impression image as the first geometric position correction.

6. The method according to claim 5, wherein the object is a portion of a bigger object; and the method further comprises the steps of:

determining a geometric position of the bigger object in the impression image;

presenting an overlay of the bigger object on the impression image; wherein the step of receiving the repositioning of the target area with respect to the impression image includes receiving a repositioning of the overlay of the bigger object with respect to the target area.

7. A method for configuring an X-ray imaging system for taking an X-ray image of an object, the method comprising the steps of:

obtaining one or more first depth images from one or more depth cameras, the one or more depth cameras covering at least an area covered by an X-ray bundle from an X-ray source;

displaying an impression image derived from the one or more first depth images on a display of a client device to a user, the impression image including a representation of the area covered by the X-ray bundle;

obtaining from the client device a first geometric position correction of the X-ray imaging system with respect to the impression image;

using the first geometric position correction to calculate an actual geometric position configuration of the X-ray imaging system based on a predetermined positional relationship between the one or more depth cameras and the X-ray imaging system; and applying the actual geometric position configuration to the X-ray imaging system; wherein the step of obtaining from the client device further includes receiving an interaction by the user with the display as the first geometric position correction;

the first geometric position correction includes a first resizing position correction;

the actual geometric position configuration includes a diaphragm configuration of the X-ray system;

the step of using includes using the first resizing position correction to calculate the diaphragm configuration of the X-ray imaging system;

the step of displaying includes displaying a target area indicative of the area covered by the X-ray bundle on the impression image; and the interaction includes a resizing operation of the target area or of the impression image performed on the display as the first resizing position correction.

8. The method according to claim 7, wherein the step of displaying includes displaying a target area indicative of the area covered by the X-ray bundle on the impression image; and the step of obtaining further includes receiving a repositioning of the target area with respect to the impression image as the first geometric position correction.

9. The method according to claim 8, wherein the object is a portion of a bigger object; and the method further comprises the steps of:

determining a geometric position of the bigger object in the impression image;

presenting an overlay of the bigger object on the impression image; wherein the step of receiving the repositioning of the target area with respect to the impression image includes receiving a repositioning of the overlay of the bigger object with respect to the target area.

* * * * *